US005679841A

United States Patent [19]
Knöfel et al.

[11] Patent Number: 5,679,841
[45] Date of Patent: Oct. 21, 1997

[54] FRACTIONATION AND PURIFICATION OF AROMATIC POLYAMINE MIXTURES AND THE USE THEREOF

[75] Inventors: Hartmut Knöfel, Odenthal; Michael Brockelt, Leverkusen, both of Germany

[73] Assignee: Bayer Aktiengesellschaft, Leverkusen, Germany

[21] Appl. No.: 623,287

[22] Filed: Mar. 28, 1996

[30] Foreign Application Priority Data

Apr. 7, 1995 [DE] Germany ............ 195 13 069.3

[51] Int. Cl.$^6$ .................................. C07C 209/86
[52] U.S. Cl. .......... 560/347; 564/315; 564/331; 564/332; 564/333; 564/334; 564/437; 564/450; 564/451
[58] Field of Search .................. 564/315, 331, 564/332, 333, 334, 437, 450, 451; 560/347

[56] References Cited

U.S. PATENT DOCUMENTS

| | | | |
|---|---|---|---|
| 4,087,459 | 5/1978 | Knöfel et al. | 564/331 |
| 4,914,236 | 4/1990 | Knöfel et al. | 564/334 |
| 4,924,028 | 5/1990 | Knöfel et al. | 564/331 |
| 5,196,591 | 3/1993 | Knöfel et al. | 564/331 |
| 5,359,141 | 10/1994 | Knöfel et al. | 564/331 |

FOREIGN PATENT DOCUMENTS

| | | |
|---|---|---|
| 31423 | 7/1981 | European Pat. Off. . |
| 161600 | 11/1985 | European Pat. Off. . |
| 2238319 | 2/1973 | Germany . |
| 1170619 | 11/1969 | United Kingdom . |

*Primary Examiner*—Richard L. Raymond
*Attorney, Agent, or Firm*—Joseph C. Gil

[57] ABSTRACT

The invention relates to a process for the fractionation and purification of aromatic polyamine mixtures and the use thereof.

11 Claims, 4 Drawing Sheets

FRACTIONATION AND PURIFICATION OF AROMATIC POLYAMINE MIXTURES AND THE USE THEREOF

BACKGROUND OF THE INVENTION

The present invention relates to a process for the fractionation and purification of aromatic polyamine mixtures and the use thereof.

Numerous patent applications and patents describe the preparation of aromatic polyamines and polyamine mixtures, in particular of the diphenylmethane series, and also the use of these products. These publications place great importance on the use of these products as raw materials for manufacturing isocyanates, generally by reacting the polyamine mixtures with phosgene by the known methods generally practiced.

However, in many cases the resulting isocyanates or isocyanate mixtures arise in forms and compositions not appropriate to their preferred further use in the isocyanate stage, which must first be converted into the appropriate usable form by, in some cases costly, working-up and separation processes. Suitable precursor polyamines which can be converted at less expense into the isocyanate forms to be used frequently give rise to process engineering problems, are completely inaccessible or are economically unattractive to manufacture.

An example is 4,4'-diisocyanatodiphenylmethane, which is important in the manufacture of high-grade polyurethane materials, the precursor amine of which is generally obtainable from aniline and formaldehyde only jointly with isomers, in particular the 2,4'-isomer, and higher-functional polyamines. Although these constituents are the foundation for isocyanates which are equally in demand, the raw isocyanates are not readily separated into those isocyanates or isocyanate mixtures which are suitable for further use.

Generally, this involves first separating some of the binuclear compounds from the remainder. The 4,4'-diisocyanatodiphenylmethane is then liberated from the other isomers from the binuclear fraction in a second distillation step which requires many separation stages.

The 2,4'-isomer in enriched form has recently itself acquired increasing importance as a raw material for polyurethane and it is only with considerable distillation effort that it can be enriched by comparison with the 4,4'-isomer and liberated from the 2,2'-isomer which is optionally present.

Isomer separation processes or enrichment processes within the fraction comprising higher-nuclear homologues or higher-functional constituents of amines and of isocyanates of the diphenylmethane series are virtually unknown.

4,4'-diaminodiphenylmethane is also gaining ground increasingly as a raw material for di-(4-isocyanatocyclohexyl)methane, the nucleus-hydrogenated form of 4,4'-diisocyanatodiphenylmethane, wherein it is very costly to prepare suitable aromatic polyamine mixtures for the hydrogenation stage having as high a 4,4'-diaminodiphenylmethane content as possible with simultaneously as low a proportion of 2,4'-diaminodiphenylmethane as possible.

It is known that amines can in some cases be separated by partially converting them into their salts, wherein, inter alia, use is made of the different base strengths. These are generally monoamines having widely differing base strengths. Such disproportionation effects have also already been described in two-phase systems in respect of aromatic polyamine mixtures, in particular of the diphenylmethane series (German Auslegeschriften 2,238,319 and 2,528,694).

As a result of the numerous components present in such a mixture, whose amino groups differ hardly at all in terms of type—virtually all are arylamino groups—the effects are not particularly sizeable or pronounced in terms of being of interest for direct use with simple means.

The object was to provide a process which enables aromatic polyamine mixtures to be fractionated and/or purified in simple manner such that isomers arise in a pure or an enriched form.

DESCRIPTION OF THE INVENTION

Figure 1:
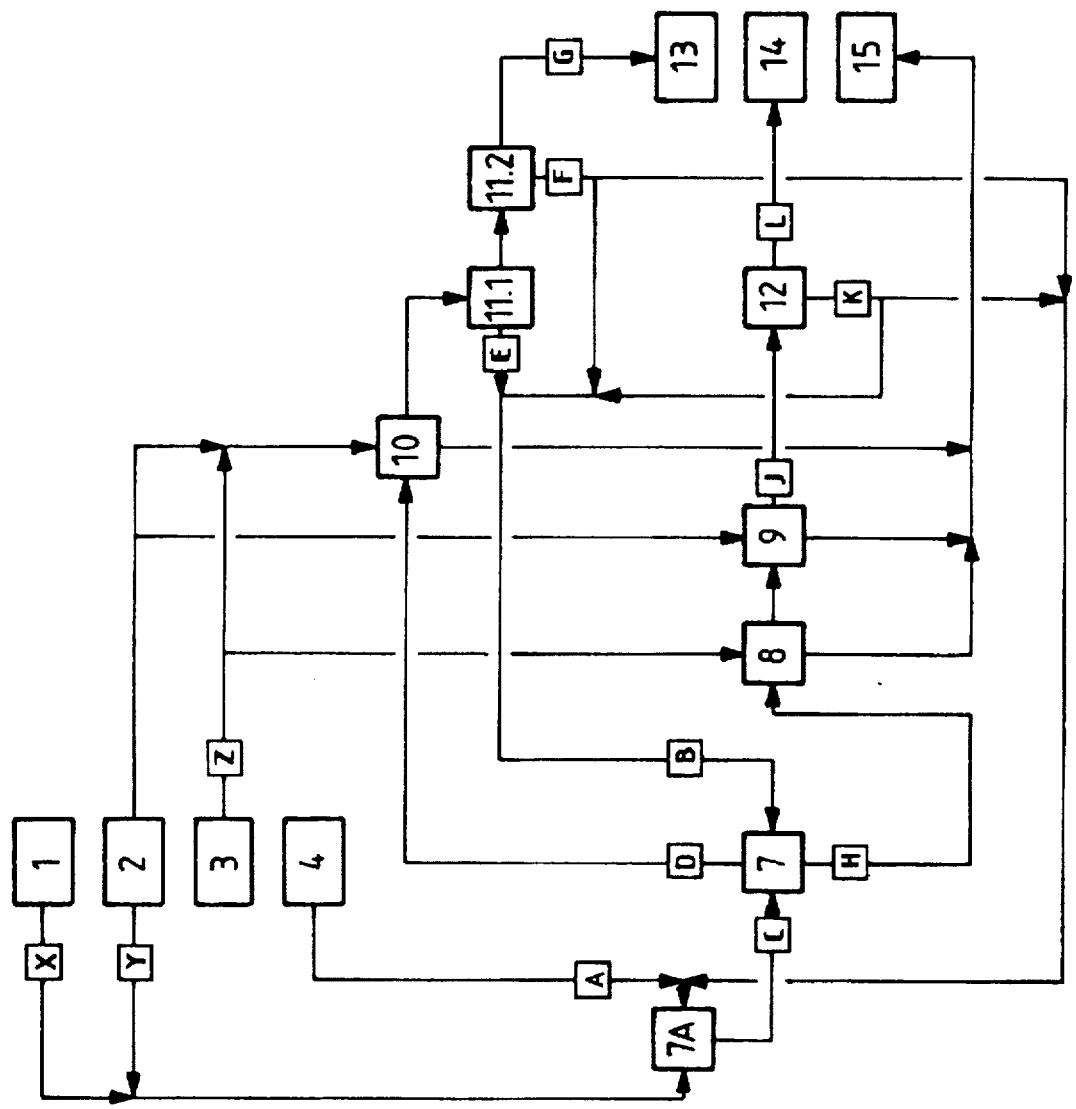
FIGS. 1 through 4 represent flow diagrams for embodiments of the present invention.

The above noted object is achieved by the process according to the invention, which attains a surprisingly high separation efficiency in the fractionation of aromatic polyamine mixtures, in particular of the diphenylmethane series, and does so in a manner which far outperforms the known effects of the prior art.

Other polyamine mixtures of various compositions are obtained during the fractionation according to the invention of aromatic polyamine mixtures. These derived polyamine mixtures may be of types which are accessible only at very great cost by known synthetic routes. They may also be polyamine mixtures which are more suitable for simpler manufacture of isocyanates than those which are known and are readily amenable to industrial preparation, in that, for example, in the amine stage they anticipate difficult isomer separations in the isocyanate stage. Such mixtures may also be completely novel polyamine mixtures because they cannot be realized using the prior art, and may lead to completely novel isocyanates.

On the other hand, the process according to the invention may be used to obtain from any—thus including recycled—polyamine mixtures product fractions which are to standard or which conform to the starting polyamines, despite the polyamine mixtures differing from the polyamines or isocyanates originally utilized as a result of impurities or non-static, i.e. selective, losses of some components.

Finally, the process according to the invention may be used to co-fractionate synthesis-related by-products and intermediates which are undesirable in the end product, and to impoverish them in one product fraction and accordingly enrich them in another, optionally to transfer them out in an independent fraction.

The present invention provides a process for the fractionation and purification of aromatic polyamine mixtures, in particular polyamine mixtures of the diphenylmethane series, which is characterized in that a) the polyamine starting mixture (A) is distributed, with intermixing of the phases, in a two-phase system comprising (i) a hydrophobic solvent phase (B) which comprises substantially hydrophobic solvent and optionally an aromatic auxiliary amine which is virtually insoluble in water and exhibits at normal pressure a boiling point which is at least 20° C. below the boiling point of the lowest-boiling component of the starting mixture and at least 20° C. above the boiling point of the solvent, and optionally polyamine, and (ii) an aqueous phase (C) comprising substantially water, a strong acid and optionally auxiliary amine present at least in part in the salt form, and optionally polyamines present at least in part in the salt form, with the use as an aid of an extraction stage (7) operating on the countercurrent principle, in that the starting polyamine mixture is introduced into the extraction stage (7) with the aqueous phase, with the proviso that in this two-phase system the sum of the amine equivalents introduced in streams (A), (B) and (C) always exceeds the number of acid equivalents introduced in stream (C), the organic phase (D) leaving this extraction stage (7) is, b) optionally at least in part by way of an interposed extraction stage (6) and/or c) optionally with separation of a partial stream upstream or downstream of the extraction stage (6) which is optionally passed through and return of the separated partial stream to the extraction stage (7) and/or to the optionally present extraction stage (6) by way of an extraction stage (5) positioned upstream, d) separated in an optionally multi-stage distillation (11.1), (11.2) into a first fraction (E) which is recycled in extraction stage (7), comprising substantially hydrophobic solvent and optionally auxiliary amine, optionally a second fraction (F) comprising substantially auxiliary amine and optionally hydrophobic solvent, and a distillation residue (G) comprising substantially a first polyamine fraction, and e) the aqueous phase (H) leaving the first extraction stage (7) is guided into a neutralization stage (8), the acid contained in the aqueous phase is neutralized with bases, preferably aqueous sodium hydroxide, and is then separated mechanically in a phase separation step into an aqueous phase containing the acid in the form of its neutral salts, and an organic phase containing substantially polyamine, optionally auxiliary amine and optionally hydrophobic solvent, and f) the organic phase (J) arising in the neutralization stage (8) is, optionally after passing through a washing stage (9), worked up at least in part in a distillation stage (12) into a distillation fraction (K) containing the proportions of hydrophobic solvent contained in (J) or (J') and the auxiliary amine optionally contained, and a second polyamine fraction arising as the distillation residue (L).

The numbers and capital letters used above and in the description which follows refer to elements and streams in the drawings.

The process according to the invention is particularly preferably carried out such that b) the organic phase (D) arising in the extraction stage (7) is extracted at least in part in an interposed extraction stage (6), in countercurrent, with at least a part volume of the aqueous acid (stream X) and/or optionally water from stream (Y) and/or optionally auxiliary amine and/or is extracted in countercurrent with at least a part volume, preferably with the total volume, of the aqueous phase (Q) arising in the optionally present extraction stage (5) positioned upstream, the aqueous phase (N) resulting in the interposed extraction stage (6) is supplied to the extraction stage (7), and the organic phase (O) arising in the interposed extraction stage (6) is supplied to the working-up stage (11).

A further improved and hence preferred embodiment of the process according to the invention is comprised in that c) a partial stream of the organic phase (D) leaving the extraction stage (7) and/or a partial stream of the organic phase (O) leaving the optionally present interposed extraction stage (6) is separated and in an extraction stage (5) positioned upstream is extracted in countercurrent with at least a part volume of the aqueous acid available as stream (X), the organic stream (P) utilized in the extraction stage (5) is dimensioned such that there takes place in (5) as extensive a transfer as possible of the polyamine contained in the said organic stream into the aqueous phase (Q), the aqueous phase (Q) resulting in the extraction stage (5) positioned upstream is, optionally after the addition of water from stream (Y) and/or auxiliary amine, supplied to the extraction stage (6), and the organic phase (R) impoverished as to polyamine and arising in the extraction stage (5) positioned upstream is supplied to the extraction stage (7) and/or to the optionally present extraction stage (6).

More particularly, the present invention, in its broadest embodiment, is directed to a process for the fractionation and purification of aromatic polyamine mixtures, in particular of polyamine mixtures of the diphenylmethane series, comprising:

a) mixing the polyamine starting mixture (A) in a first extraction stage (7) with a two-phase system comprising (i) a hydrophobic solvent phase (B) which consists essentially of hydrophobic solvent and optionally an aromatic auxiliary amine which is substantially insoluble in water and exhibits at normal pressure a boiling point which is at least 20° C. below the boiling point of the lowest-boiling component of the starting mixture and at least 20° C. above the boiling point of the solvent, and optionally polyamine, and (ii) an aqueous phase (C) consisting essentially of water, a strong acid and auxiliary amine present at least in part in the salt form, and optionally polyamines present at least in part in the salt form, with said first extraction stage (7) operating on the countercurrent principle, and wherein said polyamine starting mixture (A) is introduced into said first extraction stage with said aqueous phase (C), with the proviso that the sum of amine equivalents introduced via polyamine mixture (A), hydrophobic solvent phase (B) and aqueous phase (C) always exceeds the number of acid equivalents introduced via aqueous phase (C), and with the further proviso that a first aqueous phase (H) and a first organic phase (D) exit said first extraction stage (6), a) distilling said first organic phase (D) in a first distillation stage (11) into i) a first fraction (E) consisting essentially of hydrophobic solvent and optionally auxiliary amine, and ii) a distillation residue (G) consisting essentially of a first polyamine fraction, c) neutralizing said first aqueous phase (H) by adding a base thereto (8) and phase separating the resultant mixture into i) a second aqueous phase containing the acid in the form of its neutral salt, and ii) a second organic phase consisting essentially of polyamine and optionally auxiliary amine and/or small amounts of hydrophobic solvent d) separating said second organic phase in a second distillation stage (12) into i) a distillate (K) consisting essentially of hydrophobic solvent and auxiliary amine, and ii) a distillation residue (L) consisting essentially of a second polyamine fraction, and e) recycling said first fraction (E) as at least a portion of said hydrophobic solvent phase (B).

Aniline and/or anilines which have alkyl substitution on the aromatic ring (nucleus) are preferably utilized as the auxiliary amines, and a polyamine mixture such as arises during acid-catalyzed aniline/formaldehyde condensation is preferably utilized as the polyamine mixture of the diphenylmethane series.

The polyamine mixtures thus treated, thus the fractions generated by the process according to the invention, are used to manufacture the corresponding aromatic polyisocyanate mixtures and to manufacture polyurethane plastics. The fractions generated by the process according to the invention may also be used to prepare the corresponding nucleus-hydrogenated polyamines or as cross-linking agents and as epoxy hardeners. The corresponding polyisocyanates prepared from the fractionated polyamine mixtures are preferably utilized to manufacture polyurethane foams.

Starting mixtures are, for example, technical grade arylamine mixtures such as arise from the starting compounds during manufacture or such as arise during recovery. Examples of starting arylamine mixtures for the fractionation and purification whereof the process according to the invention is particularly suitable are:

1. polyamine mixtures of the diphenylmethane series, such as occur during condensation and acid-catalyzed rearrangement of aniline with formaldehyde,
2. polyamine mixtures of the diphenylmethane series such as arise during acid-catalyzed condensation of substituted anilines with formaldehyde,
3. polyamine mixtures of the diphenylmethane series such as arise during co-condensation of substituted anilines with one another and/or with anilines with formaldehyde,
4. polyamine mixtures of the diphenylmethane series such as arise during condensation, including co-condensation, of substituted anilines and/or aniline with aldehydes and/or ketones,
5. polyamine mixtures of the diphenylmethane series such as occur during the nitration and subsequent reduction of di- and/or polyarylmethanes and/or substituted di- and/or polyarylmethanes; the term polyarylmethanes is in this instance understood to refer to the benzyl homologues of diphenylmethane in particular,
6. polyamine mixtures of the diphenylmethane series such as occur during condensation of monoaryl monoamines (e.g. aniline, substituted anilines) and/or monoaryl diamines (phenylenediamines, substituted phenylenediamines) with aldehydes, ketones in particular formaldehyde, and acid-catalyzed rearrangement and
7. polyamine mixtures of the triphenylmethane series such as occur, for example, during the nitration and subsequent reduction of triphenylmethanes and the higher-nuclear, in particular benzyl, homologues thereof.

The hydrophobic solvents which are utilized are inert solvents within the boiling point range 30° to 280° C., preferably 80° to 200° C., such as, for example, chlorobenzene, dichlorobenzene, benzene, toluene, ethylbenzene, cumene, xylene, dichloroethane, chloroform and carbon tetrachloride. Xylenes, that is to say technical grade xylene mixtures, in particular o-xylene, toluene, ethylbenzene, cumene and chlorobenzene are preferably utilized. Solvents such as exhibit a good dissolving power in respect of the polyamine mixtures utilized are preferably used.

The acids utilized are water-soluble proton acids having a pKA value of less than 2.5, preferably less than 1.5. Examples are hydrochloric acid, hydrobromic acid, sulfuric acid, trifluoroacetic acid, methanesulphonic acid or phosphoric acid. Hydrochloric acid and sulfuric acid are preferably utilized. The acids named may also be utilized in mixture with acid or neutral salts of such acids, such as, for example, the corresponding ammonium salts or equally the corresponding alkali metal salts. The named acids are generally present in the aqueous phase (C) either as an aqueous solution of the free acid or as an aqueous solution which contains, in addition to the free acid, also the ammonium salts of the acid with auxiliary amine and/or polyamine, or as an aqueous solution in which the acid is present completely in the form of its ammonium salts with auxiliary amine and/or polyamine, and which contains optionally further auxiliary amine and/or polyamine not bound in the salt form.

At the latest after passing through the extraction stage (7), the named acids are present in the aqueous phase in the form of the ammonium salts of the acid with the polyamine fraction which is contained in the aqueous phase and optionally with auxiliary amine.

After passing through the extraction stage, optionally the extraction stages, the acid contained in the aqueous phase is converted into the corresponding neutral salts by neutralization with strong bases. This liberates the polyamines which are bound in salt form and optionally auxiliary amine.

Monoarylamines or mixtures of monoarylamines such as aniline and/or aniline derivatives having alkyl substitution on the ring and/or on the nitrogen atom are generally used as the auxiliary amine. Primary anilines are preferred, and in addition to aniline 2,6-dimethylaniline, xylidine mixtures and 2-methyl-6-ethylaniline are particularly preferred.

The process according to the invention may be carried out both batchwise and continuously. A preferred embodiment is the continuous mode, in which the process is carried out in all stages under the pressure inherent in the system and preferably in an inert gas atmosphere (nitrogen).

Figure 2:
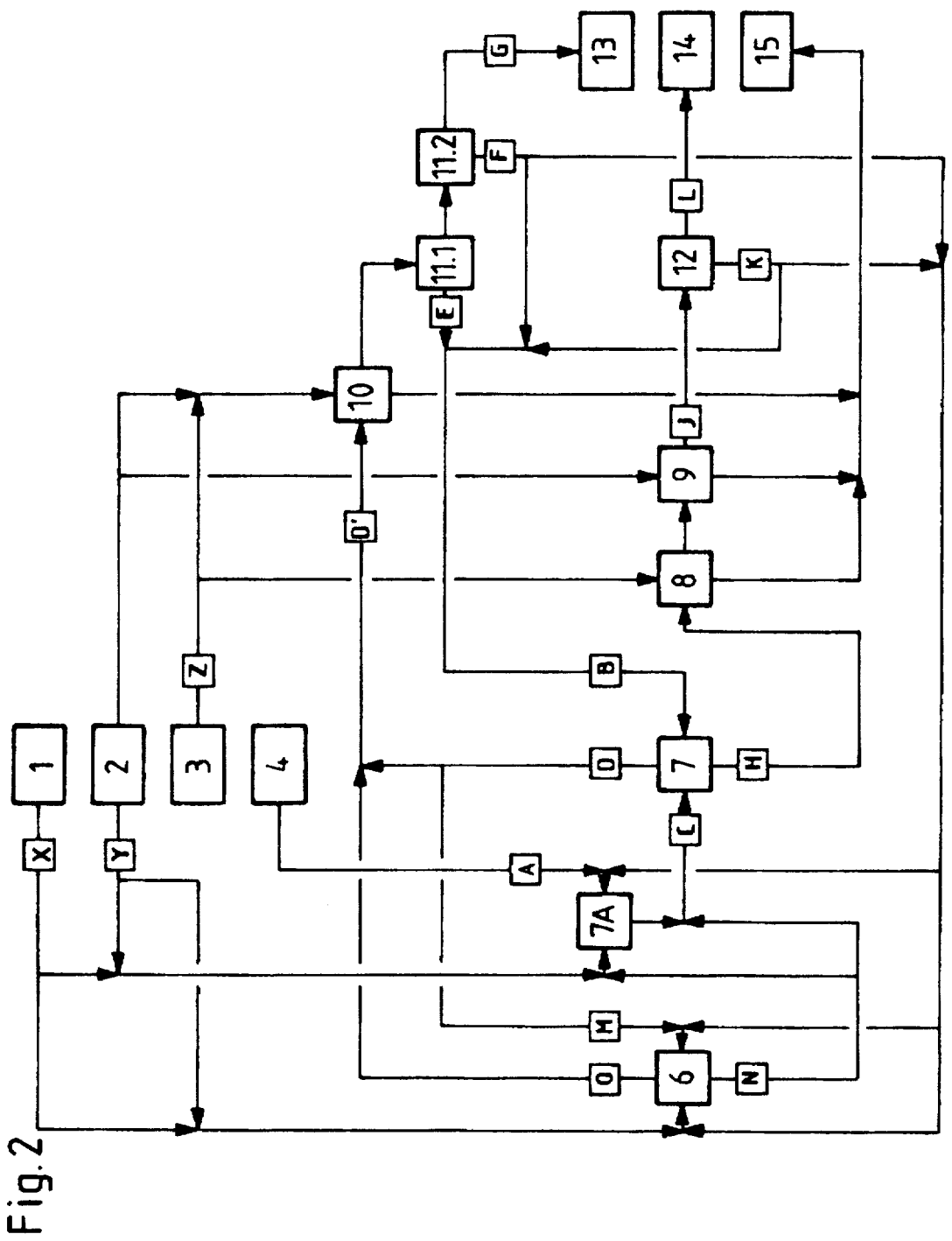
Figure 3:
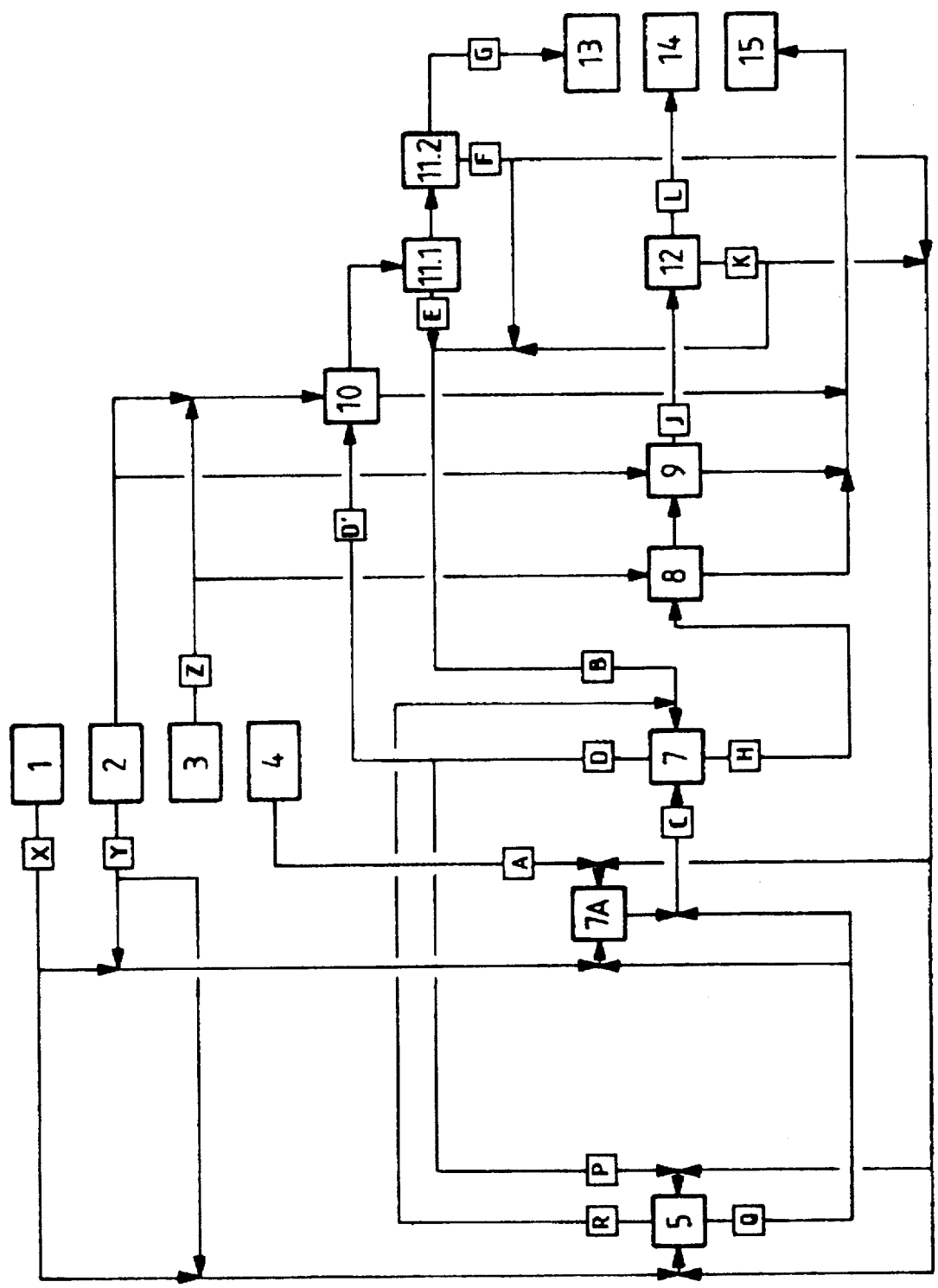
Figure 4:
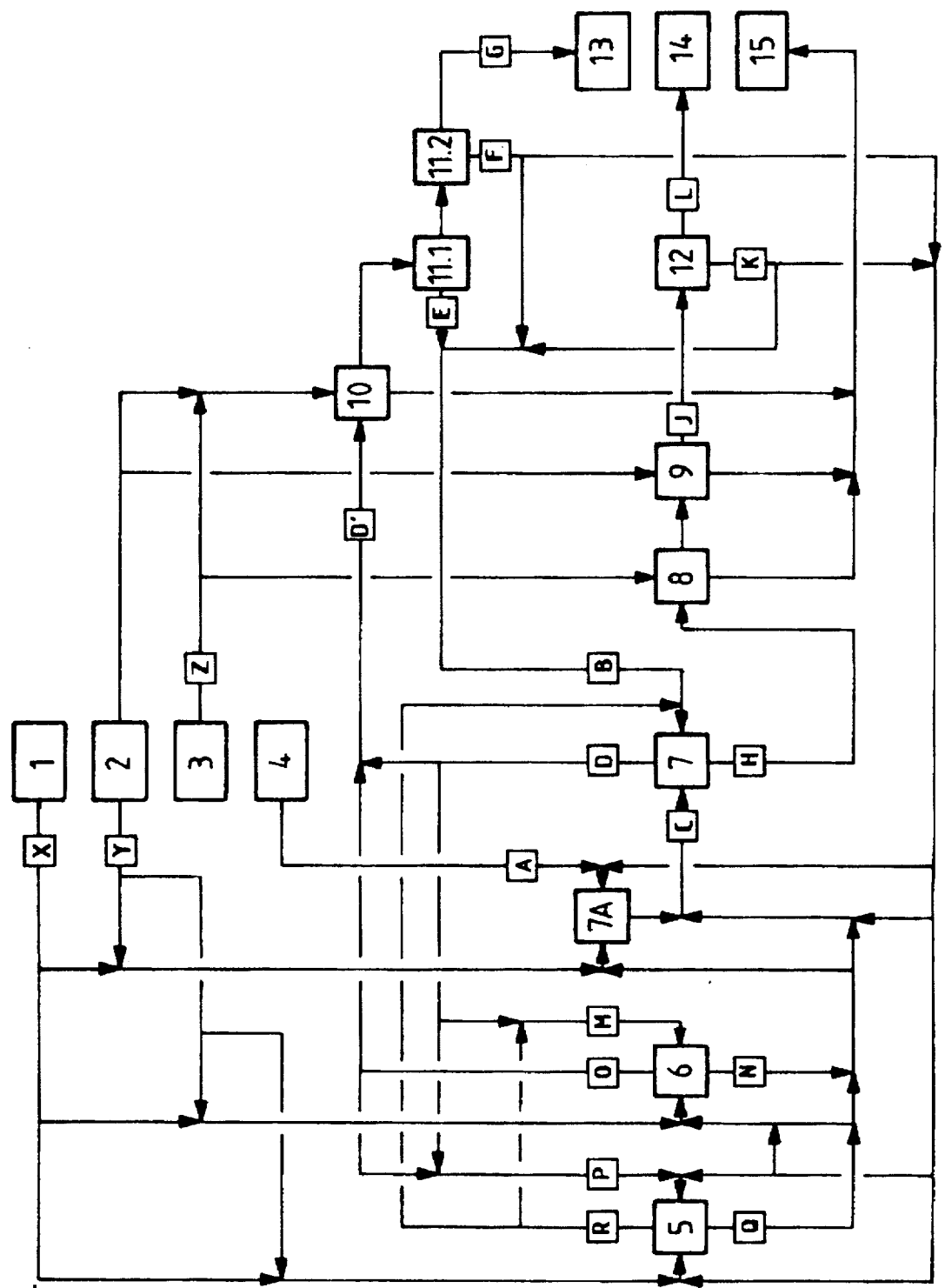

The process according to the invention may be carried out both with one (FIG. 1), with two (FIGS. 2 and 3) or three (FIG. 4) extraction stages.

The process according to the invention may be repeated with each of the product fractions arising in order to increase the enrichment or corresponding impoverishment effect.

The flow diagrams of FIGS. 1 through 4 serve to explain further the process according to the invention, with the following references:

(1) a tank for aqueous acid
(2) a tank of water
(3) a tank for aqueous base
(4) a tank for starting polyamine
(5) a single- or multi-stage extractor whereof the, from the point of view of the aqueous phase, first, stage generally comprises a mixer-settler unit.
(6) an extraction stage
(7A) a mixer or a mixer-settler unit
(7) an extraction stage
(8) a neutralization stage
(9) a washing stage
(10) a washing stage
(11.1) a first distillation stage of an optionally multi-stage distillation
(11.2) a final distillation stage of an optionally multi-stage distillation

(12) a distillation stage

(13) a tank for a first process product

(14) a tank for a further process product.

(15) a tank for effluent.

Reference letters A–R and X–Z designate the streams to which reference is made below and in the Examples.

The extraction stage (5) positioned upstream is in the simplest case a mixer-settler unit acting in single-stage manner, however extraction units acting in multi-stage manner are preferably utilized, wherein the, from the point of view of stream (X), first, stage generally comprises a mixer-settler unit.

The extraction stage (6) is in the simplest case a mixer-settler unit acting in single-stage manner, however extraction units acting in multistage manner are preferably utilized.

Stage (7A) is in the simplest case a mixer or a mixer-settler unit which is optionally positioned upstream of the subsequent extractor (7).

The extraction stage (7) likewise comprises in the simplest case a mixer-settler unit, however here too extraction units acting in multi-stage manner are preferably utilized.

The extraction units acting in multi-stage manner may comprise a plurality of extractors in series. The conventional countercurrent extraction apparatus are preferably used.

The neutralization stage (8) is constituted by an apparatus for intensive intermixing of the aqueous phase (H) in order to react the acid contained with the aqueous solution of a strong base (2) from tank (3), which is in excess, with the possibility of removing heat of neutralization and subsequent separation of the polyamine.

In the simplest case one or more stirred tanks are utilized for intermixing, and this operation may be reinforced by mixer nozzles, intensive mixers and/or forced circulation apparatus. The phase separation which follows in the simplest case utilizes separators, wherein the phase separation may be reinforced by installing separation aids. Centrifuges, for example, are also suitable.

In cases in which it is difficult or impossible to effect simple mechanical separation after the reaction between the aqueous phase (H) and strong bases, the separation is carried out by utilizing additional hydrophobic solvent and/or auxiliary amine, optionally as an extraction operation in an extractor preferably acting in multi-stage manner.

The washing stage (9) is in the simplest case a mixer-settler unit in which the stream (J) is washed with water, the washing stage (9) is not fundamentally necessary in order to carry out the process according to the invention, but is generally advantageous.

The washing stage (10) is also in the simplest case a mixer-settler unit, however extractors acting in multi-stage manner are preferably utilized. The washing stage (10) may be carried out both with water and also preferably with dilute aqueous solutions of strong bases.

The distillation stage (11) comprises in the simplest case a distillation column with which the intake product is separated into a distillate fraction (E) containing the hydrophobic solvent and optionally present auxiliary amine, and the distillation residue (G) comprising a first polyamine fraction.

When auxiliary amine is co-used the distillation stage (11) preferably comprises a multi-stage distillation having at least two stages, wherein the first stage (11.1) delivers as the distillate (E) a hydrophobic solvent which compared with the intake product is liberated from polyamine and is impoverished as to auxiliary amine, and wherein the final stage (11.2) delivers as the distillate (F) an auxiliary amine liberated from polyamine and impoverished as to solvent.

The first fraction of the starting polyamine (A) contained in stream (D) additionally arises as the distillation residue (G) in the final distillation stage (11.2).

When auxiliary amine is co-used it is not necessary for the hydrophobic solvent and the auxiliary amine to be separated completely by distillation when carrying out the process according to the invention.

The distillation stage (12) comprises in the simplest case a distillation column. When carrying out the process according to the invention without co-use of an auxiliary amine, the intake product (J) contains in the simplest case only small quantities of hydrophobic solvent. When hydrophobic solvent and/or auxiliary amine are added before or during the neutralization stage, however, these must be separated again in (12).

When carrying out the neutralization stage (8) with co-use of additional auxiliary amine, the intake product to the distillation stage (12) generally contains considerable proportions of hydrophobic solvent which are generally separated together as the distillate fraction (K) from the second polyamine fraction (L) arising as the distillation residue.

If carrying out the neutralization stage (8) necessitates the utilization of hydrophobic solvent in (8) and/or (9), even with co-use of auxiliary amine, for example in order to improve the neutralization reaction or to facilitate subsequent phase separation, then the distillation stage (12) is also carried out preferably in at least two-stage manner in order to obtain a distillate (K) in the final stage (12.2) (not illustrated here), which is impoverished to an extensive degree as to hydrophobic solvent.

Also for reasons of better energy use the distillation stages (11) and (12) are preferably carried out in multi-stage manner.

The process according to the invention may be carried out both with use of hydrophobic solvent alone and also with use of hydrophobic solvent and auxiliary amine.

The process according to the invention may be carried out in a number of technical variants.

According to a first variant, the starting polyamine mixture (stream A) is fed from the tank (4) into the process stage (7) by mixing with the aqueous stream (C), optionally by way of a stage (7A) positioned upstream.

The optionally present stage (7A) serves to relieve the extraction stage (7) and in the simplest case of the first variant of the process according to the invention comprises, positioned upstream of the stage (7), a mixer in which the stream (C) proper is formed and is adjusted from aqueous acid (stream X), optionally water (stream Y) to adjust a desired acid concentration, and/or optionally auxiliary amine.

It has proved to be advantageous also to mix already in the mixer (7A) at least part of the starting polyamine (A) with the constituents of stream (C) and to supply the aqueous phase resulting in this instance to the extraction stage (7) as an enlarged stream (C) generally comprising water, a strong acid, polyamine and optionally auxiliary amine.

The acid in the aqueous phase (C) is generally present as an aqueous solution of the acid, which optionally contains ammonium salts of the acid with auxiliary amine and/or polyamine; the acid is preferably present as an aqueous solution of its ammonium salts with auxiliary amine and/or polyamine, which optionally contains free auxiliary amine and/or polyamine, that is to say not bound in the salt form.

It has proved to be expedient to define the acid content of the aqueous phase in a manner independent of the amine content which adjusts depending on process parameters (for example, composition of the organic and the aqueous phase, phase ratio, temperature) in the aqueous phase of a two-phase system, by way of what is known as a "molarity".

The molarity is fixed as the theoretical concentration of amine which is 100% protonated (that is to say equal numbers of acid and amine equivalents) in a volume of aqueous phase, which is reduced computationally by the proportion of non-protonated amine or optionally in a volume of aqueous phase, which is enlarged computationally by a corresponding amine volume up to complete bonding of the acid as ammonium salts.

The molarity thus defined can assume values of up to 6 and, depending on the separation task which forms the basis for the embodiment in each case—in this instance, product-related—is varied in targeted manner within this range.

The acid content of the stream (C), which is well-defined and is dimensioned and controlled within narrow limits for the respective embodiment of the process according to the invention, being an important operational variable, is varied overall or in individual process stages in targeted manner within a broad range depending on the separation talk which forms the basis for the embodiment in each case in this instance product-related—optionally with the supplying of water from stream (Y) or of aqueous acid from stream (X).

This operational range has a practical upper limit, on the one hand as a result of the increasing tendency of the amine salts to crystallize as concentration increases, in particular in the case of high degrees of protonation, and on the other, as a result of the increasing mutual solubility of the phases in one another, in particular at low degrees of protonation. The degree of protonation reflects the ratio of acid equivalents to amine equivalents. This range has an economic lower limit as a result of the decreasing acid content and hence the quantitative drop in separation efficiency, that is to say when the separation efficiency is excellent and there are no technical difficulties, an increasingly large volume of aqueous phase is necessary in order to separate a given amine volume as molarity falls.

In the extraction stage (7) which is preferably operated in multistage manner, the organic phase (B) and the aqueous phase (C) are guided one towards the other with intimate intermixing.

In this operation there generally takes place a transfer of polyarylamine from the aqueous phase (C) into the organic phase (B), optionally in exchange for arylamine in the opposite direction.

It is a precondition of the transfer of polyarylamine from the introduced aqueous phase into the organic phase that the sum of the amine equivalents introduced in the streams (A), (B) and (C) always exceeds the number of acid equivalents introduced in the stream (C).

Under this precondition the organic phase (B) may in an extreme case comprise solely hydrophobic solvent and lead to a good separation result. There must in this case be present in the aqueous phase introduced into the stage (7) an excess of amine equivalents over acid equivalents.

If the organic phase (B) contains sufficient proportions of auxiliary amine and/or polyamine in addition to hydrophobic solvent, good separation results can also be achieved when there is introduced into stage (7) an aqueous phase in which the amine equivalents are present in deficit with respect to the acid equivalents.

It is naturally also possible to obtain a desired separation result with an excess of amine equivalents over the acid equivalents in the introduced aqueous phase and simultaneously an organic phase (B) which in addition to hydrophobic solvent contains auxiliary amine and/or polyamine.

It is moreover possible to carry out the process stage (7) and the process according to the invention as a whole without the use of auxiliary amine. In this event it is particularly advantageous and hence preferred to add the polyamine which has been separated as the second product fraction (L) to the organic phase (B) as optionally contained polyamine.

The organic phase (B) generally comprises hydrophobic solvent and optionally auxiliary amine and/or polyamine, the latter preferably having the composition of the second process part product (L).

When carrying out the process according to the invention without the use of auxiliary amine, stream (B) is in the simplest case formed from the distillate flow (E) of the distillation stage (11) which is in this case optionally single-stage. The stream (E) comprises in this case virtually hydrophobic solvent. In this case the effectiveness of process stage (7) is linked to there being in the introduced aqueous phase a sufficiently large excess of amine equivalents over acid equivalents, that is to say the degree of protonation in the enlarged aqueous phase (C) on which stream (A) impinges must be less than 100%.

This requirement is no longer binding when the organic phase (B) supplied to stage (7) itself contains polyamine, that is to say when more amine equivalents than acid equivalents are introduced into stage (7) with phases (C) and (B) together.

To add to the organic phase (B) polyamine in the form of starting polyamine admittedly increases throughput, however generally in terms of quality it affords a separation result which, when stage (7) is multi-stage, is largely controlled and limited by the distribution equilibrium which becomes established between the polyamine components in the supplied organic phase (B) and the aqueous phase (H) leaving stage (7).

In terms of the quality of the separation result, it is considerably more effective, and is therefore a preferred embodiment, to utilize in the absence of auxiliary amine an organic phase (B) which contains the polyamine which is separated with the aqueous phase (H) and arises as the second product fraction (L).

The organic phase (B) is in this case formed by the addition of a part volume of (L) to (E), preferably as a partial stream of the organic phase (J) leaving the washing stage (9).

Because the ammonium salts of the polyamines have an increased tendency to crystallize, in particular in the absence of auxiliary amine, the extraction stage (7) is generally operated at elevated temperatures, preferably at temperatures above 80° C., optionally under pressure, in the absence of auxiliary amine.

The starting polyamine (A) introduced into the extractor (7) together with the aqueous phase (C) is distributed between the aqueous phase (H) leaving the extractor and the organic phase (D) leaving the extractor (7) (quantitative fractionation).

In terms of volume, the individual components of the starting polyamine mixture are distributed between the resulting aqueous phase (H) and the resulting organic phase (D) with a selectivity which is surprisingly high, under the conditions of the process according to the invention, such that the resulting product fractions exhibit a different composition Which under some circumstances deviates markedly from that of the starting polyamine mixture (qualitative fractionation).

For example, taking as a basis the aniline/formaldehyde condensation products which are preferably utilized, it has been found that in the case of a polyamine component contained in the starting mixture in two or more isomeric forms, generally the ortho-isomeric form or forms thereof in the organic phase (D) leaving the separation stage (7) is/are relatively enriched; for example, 2,4'-diaminodiphenylmethane relative to 4,4'-diaminodiphenylmethane. The resulting aqueous phase (H) is, vice versa, relatively impoverished as to the 2,4'-isomer, whereas the 4,4'-isomer is relatively enriched.

If a number of "ortho-isomers" are present in the starting polyamine, for example 2,2'-and 2,4'-diaminodiphenylmethane, then the "ortho-richer" 2,2'-isomer in the organic phase (D) is more strongly enriched than the "ortho-poorer" 2,4'-isomer, which latter is, for its part, relatively enriched as compared with the "even more ortho-poor" 4,4'-isomer.

The enrichment and impoverishment effect first found with the aniline/formaldehyde condensation products of the diaminodiphenylmethane series has been linked in a purely empirical-descriptive way with the criterion of ortho- and para-substitution. The characterization of the process products which is derived from this as "ortho-rich" and "ortho-poor" is here relative and has been expressed by the concept of the "degree of ortho-substitution".

Here, the ratio of the amino groups in the ortho position proportional to the methylene groups to the total number of all the amino groups as a proportion is defined as the "degree of ortho-substitution". This concept can cover virtually all the isomer separations in the polyamines prepared from arylamines, including substituted arylamines, with carbonyl compounds in an aqueous acid medium.

The same enrichment and impoverishment effect—ordered according to the degree of ortho-substitution—has now surprisingly also been found in respect of the well characterized and analytically identifiable isomeric tri-nuclear compounds from aniline/formaldehyde condensation.

The same applies to separation of condensation products of formaldehyde with aniline and diaminoaryl compounds such as phenylenediamine or alkyl-substituted phenylenediamines.

The polyamine mixtures mentioned thus far exhibit, by virtue of their method of preparation, amino groups which are virtually only in the ortho and/or para position to methylene groups.

In this case within a group of isomeric compounds it is generally those having the higher degree of ortho-substitution which are enriched during fractionation in the organic phase (D), compared with the isomers having a lower degree of ortho-substitution.

Polyamine mixtures in particular of the diphenylmethane series, including the respective higher-nuclear homologues, which are prepared by other processes, for example by the nitration of diphenylmethane or methyldiphenylmethanes followed by reduction, also exhibit other amino group-methylene group relations in addition to amino groups in the ortho and para positions, by virtue of their method of preparation. The process according to the invention is equally effective for these polyamine mixtures.

For example, nitration and subsequent reduction can be used to prepare from a mixture of 2- and 4-methyldiphenylmethane a polyamine mixture which principally constitutes an isomer mixture of

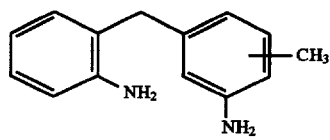

and

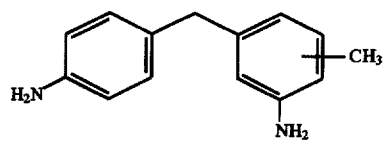

Fractionation of such mixtures with the aid of the process according to the invention enriches the 3,2'-isomers in the organic phase (D), compared with the 3,4'-isomers.

Not all the isomers in these polyamine mixtures still fit the criterion of "ortho-rich" and "ortho-poor" or of the degree of ortho-substitution, which should therefore be applied by analogy, by classifying the isomers into those having a smaller (=ortho−) and those having a greater (=para−) spatial distance between the—generally to be found on different six-membered rings—amino groups and the methylene bridge or between the amino groups themselves, in place of the terms "in the ortho position" and "in the para position".

A further class of aromatic polyamine mixtures which can be fractionated very effectively with the aid of the process according to the invention is constituted by the polyamines of triphenylmethane and the higher-nuclear homologues of triphenylmethane, preferably benzyl homologues, such as are prepared, for example, by the nitration and subsequent reduction of the corresponding hydrocarbon mixtures.

When fractionating technical grade polyamine mixtures of the lastmentioned class of substances I. co-condensation products of mono- and diaminoaryl compounds with formaldehyde or general carbonyl compounds, II. polyamine mixtures from processes involving the nitration and subsequent reduction of diphenylmethane and preferably substituted, in particular alkyl-substituted, diphenylmethanes and the respective homologues and III. polyamine mixtures from processes involving the nitration and subsequent reduction of triphenylmethane and preferably substituted, in particular alkyl-substituted, triphenylmethanes and the respective higher-nuclear benzyl homologues a further surprising selectivity has been found in addition to the pure isomer separation.

Polyamine mixtures of the named substance classes I to III contain or may contain components in which at least one aryl ring carries per molecule more than one, generally two, amino groups. These components can be the preferred constituents of the polyamine mixture, without by virtue of the process being necessarily the principal products in volume terms.

In order better to characterize such components, the concept "degree of amino substitution" is used, which primarily characterizes the number of amino groups of a component in relation to the number of aryl rings. In the case of aniline and condensation products thereof with formaldehyde, this expression is always 1.0, and for phenylenediamine and condensation products thereof is always 2.0. In the case of pure co-condensates the value is 1.5 for the diphenylmethane isomers and between >1.0 and <2.0 for the higher-nuclear homologues. Likewise values of between 1.0 and 2.0 result if the concept "degree of amino substitution" is used in random manner to characterize technical grade polyamine mixtures.

In fractionating polyamine mixtures having a degree of amino substitution of >1.0 it has now been found that the components having a higher degree of amino substitution are relatively enriched in the aqueous phase resulting in the actual separation step, in fact the more markedly the greater the degree of amino substitution.

Consequently, the process according to the invention also opens up for this substance class the possibility of decoupling the manufactured form of the raw materials (amine stage) and the used form of the end products (isocyanate stage), such as to facilitate the optimization of both stages separately up to and including obtaining completely new isocyanate mixtures.

These "achievements" are complemented by a further criterion of selectivity which has been found when fractionating technical grade polyamine mixtures, in particular those having higher-nuclear homologues, and relates to the "nuclearity" of the polyamine mixtures.

The term "nuclearity" primarily expresses the number of aryl units of a component of an aromatic polyamine mixture. In the broad sense, the concept of nuclearity is used in order to express as a random value a nuclearity of the total mixture where a polyamine mixture comprises numerous components each having its own precise nuclearity.

It has now been found particularly surprisingly when fractionating polyamine mixtures having higher-nuclear constituents, in particular when fractionating technical grade mixtures of aniline formaldehyde condensates, that the higher-nuclear components can, in targeted manner, be both relatively enriched and also relatively impoverished in the organic phase leaving the fractionation stage, in dependence on the molarity of the aqueous phase in the extraction stage (7).

A high molarity of the aqueous phase in (7) within the indicated molarity range leads to a relative impoverishment of higher-nuclear components in the organic phase (D) and accordingly to a relative enrichment in the aqueous phase (H).

A low molarity of the aqueous phase in (7) within the indicated molarity range leads to a relative enrichment of higher-nuclear components in the organic phase (D).

The surprising finding can be expanded and rendered more specific in that the relative enrichment and impoverishment also take place within the higher-nuclear homologues among themselves. If, for example, in a technical grade mixture of diaminodiphenylmethane, the trinuclear components in the one fraction are enriched or impoverished relative to the binuclear components, then a relative enrichment or impoverishment of tetranuclear components relative to trinuclear components, i.e. an even more marked relative enrichment or impoverishment, is found, and so forth in the case of pentanuclear components relative to tetranuclear components, etc.

This and the isomer separation which takes place simultaneously and always in the sense of a relative reinforcement of the "degree of ortho-substitution" in the organic phase (D), and the possibility of repeating with individual product fractions the separation according to the invention, optionally with changed process parameters, gives rise to numerous possibilities for gaining access, by way of the process according to the invention, to less readily accessible polyamines, and hence polyisocyanates, or to those which, not having hitherto been accessible according to the prior art, would be completely novel, starting from known and readily accessible polyamine mixtures. This applies particularly to products of the diamino- and diisocyanatodiphenylmethane series and quite particularly to polyamine mixtures and polyisocyanate mixtures having an extremely high proportion of higher-nuclear components.

The enrichment and impoverishment are generally more effective as the degree of protonation in the aqueous phase of the separation stage increases.

Furthermore, the process according to the invention proves also to be generally effective with other polyamines of similar structure. Thus, for example, the polyamine mixtures already mentioned, which are obtained by the nitration of di- and polyarylmethanes followed by reduction, may also contain monoaminopolyarylmethane compounds or components in which one or more methylene groups have been converted by side reactions into keto- and/or hydroxymethylene groups and thus into undesirable by-products.

Numerous incompletely rearranged intermediate compounds and by-products can occur when condensing arylamines with carbonyl compounds.

During fractionation of the polyamine mixtures which contain these compounds, the majority are generally subject to an enrichment in one of the resulting fractions, such that the effect can be used for separation and fractionation.

Such products may optionally be enriched in this way, or they may be fractionated in their own right as intentionally prepared polyamine mixtures, such as for example polyaminobenzophenones or aminobenzyl arylamine mixtures.

The organic phase (D) leaving the extraction stage (7) still contains, inter alia, small quantities of acid, generally and depending on the process parameters in the extraction stages (6) and (7) between 0.01 and 0.5 wt-%, which are advantageously removed before the stream (D) is worked up by distillation.

In the simplest case this takes places by neutralization with excess dilute aqueous bases, for example dilute sodium hydroxide.

The organic phase (D) is at least in pad transferred into the distillation stage (11), optionally after passing through the washing stage (10).

In the final stage of the optionally multi-stage distillation stage (11) the first polyamine part product (G) is separated and is collected in the process product tank (13).

The corresponding second part product is to be found in the aqueous phase (H) leaving the extraction stage (7).

The aqueous phase (H) is, optionally after the addition of auxiliary amine and/or hydrophobic solvent, reacted in the neutralization stage (8) with the aqueous solution of a strong base, preferably concentrated sodium hydroxide, in order to neutralize the acid contained.

The aqueous phase formed in the neutralization is separated and is collected in the effluent tank (15).

The organic phase formed in the neutralization is separated as stream (J), and is at least in part supplied to working-up (12) by distillation, optionally washed with water in the washing stage (9).

In the final stage of the optionally multi-stage distillation stage (12) the second polyamine part product (L) is separated and is collected in the process product tank (14).

This first variant of the process according to the invention affords the opportunity for considerable separation efficiencies in the fractionation of polyamine mixtures and enables numerous separation problems to be resolved in a satisfactory way.

In particular in the second polyamine fraction (L) the relative enrichment of the components preferably contained in this fraction can be varied and maximized in targeted manner.

The proportion of these components remaining in the first polyamine fraction (G) cannot, however, be minimized in the same way according to this first variant, but may be impoverished relatively in variable manner only up to a content whereof the lower limit depends on the distribution equilibrium of the polyamine components of (A), which is characteristic of the respective process parameters, between the organic phase (D) on leaving the extractor (7) and the aqueous phase (C) on entering the extractor (7).

The organic phase (B) generally comprises, in addition to hydrophobic solvent, optionally auxiliary amine and/or polyamine, the latter preferably having the composition of the second process part product (L).

When using an organic phase (B) without polyamine there results in the aqueous phase (H) leaving the extraction stage (7) a polyamine fraction in which the relative enrichment of the components preferably contained in this phase can be increased and maximized in targeted manner, at the expense of the polyamine concentration in the aqueous phase.

The effect of polyamine as a constituent of the organic phase (B) is to cause the phase (H) leaving the process stage (7) to exhibit a higher polyamine concentration, which is hence more advantageous in energy terms for carrying out the process according to the invention, than is the case when an organic phase (B) without polyamine is used.

As a result of the, preferred, use of a polyamine having the composition of the second part product (L) as a constituent of the organic phase (B), the relative enrichment of the polyamine components preferably contained in the aqueous phase (H) leaving the separation phase (7), and hence of the second polyamine fraction (L), can also be varied and maximized at a higher and hence more advantageous concentration level as a result of an equilibrium becoming established, with the separation effect being self-reinforcing.

A second variant of the process according to the invention is more advantageous and is a preferred embodiment; in this, in the first polyamine fraction (G) too, it is additionally possible to increase considerably and to vary in targeted manner the relative enrichment of the components preferably contained in this fraction, in that the organic phase (D) which arises in the extraction stage (7) is extracted at least in part in an extraction stage (6) which is, from the point of view of phase (D), interposed, with an aqueous phase which in the present case of variant 2 comprises substantially at least a part volume of stream (X) and optionally additional water from stream (Y).

For formal reasons the organic phase supplied to the extraction stage (6) is designated stream (M) even if it optionally matches stream (D) at least in composition, but preferably also in volume, as embodied by way of example in the present case.

Carrying out the extraction stage (6) even only in single-stage manner, for example as a mixer-settler unit, results in a markedly further relative enrichment in the resulting organic phase (O), dependent on the type and in particular the volume of the aqueous phase utilized, of those components already enriched in (D) as compared with starting polyamine (A), combined with a reduction in the polyamine content of the resulting organic phase (O). Preferably, however, the interposed extraction stage (6) is also embodied as an extractor acting in multi-stage manner and operated in countercurrent, this being more effective.

The aqueous phase (N) arising in the extraction stage (6) contains the corresponding other fraction of the polyamine introduced with stream (M), in which fraction the components enriched in (O) are correspondingly impoverished. The extent of relative impoverishment, that is to say the composition of the polyamine contained in (O), is controlled under the respective process conditions of the extraction stage (6) acting in multi-stage manner, by the qualitative and quantitative distribution equilibrium between the organic phase (M) supplied and the aqueous phase (N) discharged.

The molarity of the aqueous phase in the extraction stage (6) is, depending on the separation task, higher than or as high as or lower than the molarity in the extraction stage (7) which is, from the point of view of the aqueous phase, positioned downstream and is regulated by the addition of acid and/or the addition or optionally the removal of water at a suitable point.

The aqueous phase (N) resulting in the process stage (6) is supplied optionally after the addition of water together with the optionally present residue of (X) to the extraction stage (7).

The organic phase (O) resulting in stage (6) is supplied together with the optionally present residue of (D) to the distillation stage (11) in order to obtain the polyamine fraction (G).

With the second variant of the process according to the invention the relative enrichment can be varied and maximized in targeted manner in both resulting polyamine fractions. In addition to this great versatility and power in terms of quality, the second process variant also represents an embodiment which is favorable as to energy at least for the second polyamine fraction (L).

The energy consumption associated with obtaining the first polyamine fraction (G), on the other hand, increases in relative terms more markedly the lower the quantitative proportion of (G), calculated on polyamine mixture (A) utilized, because the remaining polyamine (G) content in the organic phase (D) and/or (O) which are/is to be worked up by distillation optionally becomes ever smaller.

An embodiment which is improved in this respect is represented by the third variant of the process according to the invention. Proceeding on the basis of the first variant, this is broadened in that the organic phase (D) leaving the process stage (7) and containing the first part product (G) in a concentration which is reduced with regard to the concentration of (A) in (C) is divided into a partial stream (D') which continues to be supplied to the working-up stages (10) and (11) with the aim of obtaining the polyamine fraction (G), and a stream (P).

The stream (P) is reacted in an extraction stage (5) positioned upstream with at least a part volume, preferably with the total volume, of the aqueous acid available as stream (X); the reaction optionally takes place as a multi-stage countercurrent extraction.

The extraction stage (5) is generally an extractor acting in multi-stage manner and operated in countercurrent, in which the supplied organic phase (P) is extracted with at least a part volume, preferably with the total volume, of the aqueous acid (X) available for recycling.

The stream (P) supplied to the extractor (5), when reacted with stream (X), is here dimensioned such that there takes place as extensive a transfer as possible, preferably virtually quantitative, at least of the polyamines contained in the organic phase (P) into the aqueous phase (Q) leaving the extractor (5).

The residual polyamine content of the organic phase (R) resulting in the process stage (5) is generally around <3 wt-%, preferably around <1 wt-%.

For the rest, the permitted maximum amine, and in particular polyamine, content permitted in (R) is determined by the quality demands made of the process products, set by the respective separation task, in the case of variant 3 in particular the demands made of the process part product (L). Maintenance of the polyamine content which is relevant to the quality of (L) is controlled within the framework of the technical factors by way of dimensioning the part stream (P), with exhaustion of the available aqueous acid (X), optionally of a volume of (Y).

Here it is useful to the process and in particular to extraction stage (5) that the aqueous acid (stream X) available for utilization in stage (5) is greater the greater the proportion of the second polyamine fraction (L) and the smaller, consequently, the proportion of the first polyamine fraction (G). A small polyamine fraction (G) generally signifies a low polyamine concentration in the organic phase (D) and a high energy consumption for working up such a phase. It is possible by means of variant 3 according to the invention, as compared with variant 1, to reduce in particular the energy consumption when isolating the first polyamine fraction (G).

The contribution which process stage (5) within the framework of variant 3 makes towards improving the process according to the invention is that for the working-up (11) by distillation to obtain the first polyamine fraction (G) there arises, instead of the total flow having a polyamine concentration which is relatively low and hence unfavorable in energy terms, only a partial stream having a concentration which is correspondingly higher and hence more favorable in energy terms (quantitative enrichment), while from the other partial stream an organic phase (R) which can be used at a suitable point as an extraction agent is obtained without distillation.

The organic phase (R) leaving process stage (5), which is largely liberated from polyamine, is supplied to the extraction stage (7).

In the extraction stage (7) which acts preferably in multi-stage manner the organic phase (R) is added as the extraction agent, generally by mixing with stream (B) and addition to the, from the point of view of the organic phase (B), first stage of the extractor.

In dependence on an optionally present residual polyamine content in (R), and having regard for the quality of the second polyamine fraction (L), the addition of the organic phase (R) is effected optionally to an extraction stage (7) which is, from the point of view of the organic phase (B), later, optionally to the final stage of the extraction stage (7) which operates in multi-stage manner.

Optionally, the addition of (R) takes place at least in part to the optionally present stage (7A) positioned upstream, which in this case is preferably operated as a mixer-settler unit. After the two-phase mixture formed in the mixer is separated, optionally only the aqueous phase is supplied to the process stage (7), the separated organic phase being added on the other hand to the partial stream of (D) which is supplied to the extraction stages (5) and/or (6).

The aqueous phase (Q) leaving the process stage (5) contains, in addition to the acid present at least in part in the form of its ammonium salts, polyamine having a composition which corresponds largely to the polyamine in the supplied organic phase (P) and optionally auxiliary amine.

In the case of variant 3 of the process according to the invention, the stream (Q) is supplied directly to the process stage (7), optionally after the addition of water from stream (Y) and/or of further aqueous acid from stream (X).

Because the polyamine fraction contained in the aqueous phase (Q) generally exhibits a higher relative (qualitative) enrichment in terms of the first polyamine fraction (G), by reference to the starting polyamine (A), the result for the aqueous phase supplied to the extraction stage (7) after the addition of starting polyamine (A) is a mixed polyamine which is "enriched" by comparison with the starting polyamine (A) in dependence on the quantitative ratio. As a result of the distribution equilibrium between supplied aqueous and resulting organic phase (D), the result for variant 3 is also a limited additional qualitative enrichment effect for the first polyamine fraction (G).

In a further variant 4 of the process according to the invention, the technical measures of the preceding variant are brought together and combined.

In the simplest case the extraction stages (5) and (6) are added and each independently carried out in the manner described, with a partial stream of (X), optionally a partial stream of (Y) and a partial stream of (D) which is in this case optionally divided into 3 partial streams.

It is more advantageous to utilize as the organic phase (P) in extraction stage (5) a partial stream of the stream (O) which contains a qualitatively highly enriched and quantitatively less concentrated polyamine fraction.

The variant 4 is preferably carried out such that as the organic phase (P) a partial stream of (D) and/or preferably a partial stream of (O) are/is utilized in the extraction stage (5), and at least part, preferably all, of the aqueous phase (Q) resulting in stage (5) is supplied to the extraction stage (6) and is utilized in (6) optionally with the addition of further aqueous acid from stream (X) and optionally of auxiliary amine. In so doing, the organic phase (M) with its content of polyamine enriched in the same way is guided towards this with intimate intermixing in several stages, optionally the organic phase (M) is strengthened by the addition to (M) of a partial stream of the organic phase (R) resulting in the extraction stage (5).

The outcome of these measures is a further increase in the qualitative enrichment effect in the organic phase (O) resulting in (6). In quantitative terms this result can be achieved in the phases which result in (6), in particular in the organic phase (O), by dimensioning and dividing the streams at a polyamine content which is relatively high and hence favorable in energy terms.

The back-coupling of the enrichment effect in (O) by way of stream (P) as a partial stream of (O) and by way of the aqueous phase (Q) here has a self-reinforcing effect.

By re-positioning the extraction stages (5) to (7) in variant (4) with process criteria such as disproportionation in place of fractionated extraction in stage (6), with self-reinforcement by re-positioning with extraction stage (5), and recovery of extraction agent in stage (5) without distillation for utilization in process stage (7) and optionally in (6), there results maximum qualitative separation efficiency which, combined with varying the molarity of the aqueous phases in stages (5) to (7), leads to a wide range of applications for the process according to the invention.

The invention is further illustrated but is not intended to be limited by the following examples in which all parts and percentages are by weight unless otherwise specified.

EXAMPLES

Example 1

There are mixed together in a mixer (7A) the starting polyamine mixture (stream A) (1.260 kg/h), aniline (0.495 kg/h) (part streams F and K), 30%- concentration hydrochloric acid (0.885 kg/h) (stream X) and water (1.860 kg/h) (stream Y), forming the aqueous stream (C).

| Stream (C) | 28.0% polyarylamine |
| (4.500 kg/h) | 11.0% aniline |
|  | 5.9% hydrochloric acid |
|  | 55.1% water |

Stream (C) is guided towards the organic stream (B) in an extractor acting in multi-stage manner at 90° C.

| Stream (B) | 37.3% aniline |
| (1.680 kg/h) | 62.2% xylene |
| | approx. 0.5% water |

The resulting organic phase (D) leaving the extraction stage (7) has the following average composition:

| Stream (D) | 23.6% polyarylamine |
| (1.865 kg/h) | 18.8% aniline |
| | 55.8% xylene |
| | <0.2% hydrochloric acid |
| | <1.6% water. |

Stream (D) is washed with excess dilute sodium hydroxide (part stream of Z and water from 2) in the neutralization stage (10). The aqueous phase is collected in tank (15) as effluent.

Stream (D), washed and liberated from acid esters, is liberated largely from xylene and part of the aniline in a first distillation stage (11.1), and from the remaining aniline and residual xylene in a second distillation stage (11.2). The two distillates (streams E and F) are combined and, together with a corresponding partial stream of (K), form stream (B).

The residue resulting in distillation stage (11) comprises polyamine mixture which is collected in tank (13) at a rate of 0.441 kg/h as stream (G).

The aqueous phase (H) leaving the extractor (7) has the following average composition

| Stream (H) | 19.0% polyarylamine |
| (4.310 kg/h) | 17.8% aniline |
| | 6.1% hydrochloric acid |
| | 57.1% water | and is neutralized with excess aqueous sodium hydroxide from tank (3) (part stream Z) in the neutralization stage (8). The aqueous, salt-containing phase is separated and collected in the effluent tank (15).

The organic phase is then washed with water from tank (2) in the washing stage (9) until largely salt-free. The washing water is likewise collected in the effluent tank (15).

The organic phase (stream J) leaving the washing stage is separated in the distillation stage (12) into a distillate fraction (stream K) and a distillation residue (stream L).

Stream (K) is divided into a partial stream (0.495 kg/h) which is supplied to the mixer (7A) and a second partial stream (0.274 kg/h) which, together with distillates (E) and (F) from distillation stage (11), forms the stream (B).

The distillation residue from (12) forms the second polyamine fraction (L) at a rate of 0.819 kg/h and is collected in tank (14).

| Polyarylamine GC: | A [wt. %] | G [wt. %] | L [wt. %] |
|---|---|---|---|
| 2,2'-diaminodiphenylmethane | 0.20 | 0.57 | — |
| 2,4'-diaminodiphenylmethane | 5.64 | 14.82 | 0.70 |
| 4,4'-diaminodiphenylmethane | 58.30 | 47.32 | 64.21 |
| N-methyl-4,4'-diaminodiphenylmethane | 0.26 | 0.58 | 0.09 |
| Σ-diaminodiphenylmethane | 64.40 | 63.29 | 65.00 |
| Σ-polynuclear polyamines | 35.60 | 36.71 | 35.00 |
| Quantitative distribution | 100% | 35.0% | 65.0% |

Example 2

There are mixed together in a mixer (7A) 1.040 kg/h starting polyamine mixture (stream A) with 0.319 kg/h aniline (part stream of K), 0.685 kg/h 30%-concentration hydrochloric acid (part stream of X) and 1.454 kg/h water (part stream of Y) and the aqueous stream (N), forming the aqueous stream (C).

| Stream (C) | 28.0% polyarylamine |
| (4.500 kg/h) | 11.0% aniline |
| | 5.9% hydrochloric acid |
| | 55.1% water |

Stream (C) is guided in an extractor (7) acting in multi-stage manner at 90° C. towards an organic phase which is formed from streams and (R).

| Stream (B) + (R) | 37.0% aniline |
| (1.693 kg/h) | 61.6% xylene |
| | 1.3% hydrochloric acid |
| | 0.1% water |

The resulting organic phase (stream D) leaving the extraction stage (7) has the following composition

| Stream (D) | 23.6% polyarylamine |
| (1.870 kg/h) | 18.8% aniline |
| | 55.8% xylene |
| | 0.2% hydrochloric acid |
| | 1.6% water | and, divided into equal pads, is supplied to the extraction stage (6) in a stream (M) (0.935 kg/h), and to the extraction stage (5) in a stream (P).

In the extraction stage (5) acting in multi-stage manner at 70° C. stream (P) is guided towards an aqueous phase which is formed from the part streams of (X) (0.200 kg/h 30%-concentration hydrochloric acid) and (Y) (0.100 kg/h water).

The phase (R) which results from this procedure and leaves stage (5) (0.538 kg/h) is virtually amine-free and comprises substantially xylene and small quantities of hydrochloric acid and water which are dissolved to saturation or are entrained.

The aqueous phase (Q) which results in (5) has the following average composition

| Stream (Q) | 31.7% polyarylamine |
| (0.697 kg/h) | 25.3% aniline |
| | 8.6% hydrochloric acid |
| | 34.4% water | and, after the addition to stream (Q) of 0.305 kg/h as a part volume of stream (Y), is supplied to the extraction stage (6) acting in multi-stage manner and is there guided at 90° C. as the aqueous phase towards stream (M) as the organic phase.

The organic phase (O) resulting in the extraction stage (6) has the following average composition:

| Stream (O) | 23.6% polyarylamine |
| (0.935 kg/h) | 18.8% aniline |
| | 55.8% xylene |
| | ≦0.2% hydrochloric acid |
| | ≦1.6% water. |

Stream (O) is washed with excess dilute sodium hydroxide (part stream of Z and water from 2) in the neutralization stage (10). The aqueous phase is collected in tank (15) as effluent.

The stream (O), washed and liberated from acid esters, is liberated from water, xylene and aniline in a distillation stage (11) (in single-stage or two-stage manner).

The residue resulting in distillation stage (11) comprises polyamine mixture which is collected in tank (13) at a rate of 0.221 kg/h as stream (G). distillate from stage (11) (0.705 kg/h) is combined with a part volume (0.450 kg/h) of the distillate flow (K) from distillation stage (12), forming stream (B)

| Stream (B)<br>(1.155 kg/h) | 54.2% aniline<br>45.2% xylene<br><0.6% water. |
|---|---|

The aqueous phase (N) leaving the extractor (6) is supplied to the mixer (7A)

| Stream (N)<br>(1.002 kg/h) | 22.0% polyarylamine<br>17.5% aniline<br>6.0% hydrochloric acid<br>54.5% water. |
|---|---|

The aqueous phase (H) resulting in the extraction stage (7) has the following average composition

| Stream (H)<br>(4.323 kg/h) | 18.9% polyarylamine<br>17.8% aniline<br>6.1% hydrochloric acid<br>57.2% water |
|---|---| and is neutralized with excess aqueous sodium hydroxide from tank (3) (part stream Z) in the neutralization stage (8). The aqueous, salt-containing phase is separated and is collected in the effluent tank (15).

The organic phase from the neutralization stage (8) is then washed with water from tank (2) in washing stage (9) until largely salt-free. The washing water is likewise collected in the effluent tank (15).

The organic phase (stream J), washed free of salt, is separated in the distillation stage (12) into a distillate fraction (stream K) and a distillation residue (stream L).

Stream (K) is divided into a partial stream (0.319 kg/h) which is supplied to the mixer (7A) and a second partial stream (0.450 kg/h) which is used to form stream (B).

The distillation residue from (12) forms the second polyamine fraction (L) at a rate of 0.819 kg/h, and is collected in tank (14).

| Polyarylamine GC: | A<br>[wt. %] | G<br>[wt. %] | L<br>[wt. %] |
|---|---|---|---|
| 2,2'-diaminodiphenylmethane | 0.20 | 0.94 | — |
| 2,4'-diaminodiphenylmethane | 5.64 | 23.95 | 0.70 |
| 4,4'-diaminodiphenylmethane | 58.30 | 36.40 | 64.21 |
| N-methyl-4,4'-diaminodiphenyl-methane | 0.26 | 0.89 | 0.09 |
| Σ-diaminodiphenylmethane | 64.40 | 62.18 | 65.00 |
| Σ-polynuclear polyamines | 35.60 | 37.82 | 35.00 |
| Quantitative distribution | 100% | 21.25% | 78.75% |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the fractionation and purification of aromatic polyamine mixtures comprising:
   a) mixing the polyamine starting mixture in a first extraction stage with a two-phase system comprising
      (i) a hydrophobic solvent phase which consists essentially of hydrophobic solvent and optionally an aromatic auxiliary amine which is substantially insoluble in water and exhibits at normal pressure a boiling point which is at least 20° C. below the boiling point of the lowest-boiling component of the starting mixture and at least 20° C. above the boiling point of the solvent, and optionally polyamine, and
      (ii) an aqueous phase consisting essentially of water, a strong acid and auxiliary amine present at least in part in the salt form, and optionally polyamines present at least in part in the salt form.
   with said first extraction stage operating on the countercurrent principle, and wherein said polyamine starting mixture is introduced into said first extraction stage with said aqueous phase, with the proviso that the sum of amine equivalents introduced via polyamine mixture, hydrophobic solvent phase and aqueous phase always exceeds the number of acid equivalents introduced via aqueous phase, and with the further proviso that a first aqueous phase and a first organic phase exit said first extraction stage,
   b) distilling said first organic phase in a first distillation stage into
      i) a first fraction consisting essentially of hydrophobic solvent and optionally auxiliary amine, and
      ii) a distillation residue consisting essentially of a first polyamine fraction,
   c) neutralizing said first aqueous phase by adding a base thereto and phase separating the resultant mixture into
      i) a second aqueous phase containing the acid in the form of its neutral salt, and
      ii) a second organic phase consisting essentially of polyamine and optionally auxiliary amine and/or small amounts of hydrophobic solvent
   d) separating said second organic phase in a second distillation stage into
      i) a distillate consisting essentially of hydrophobic solvent and auxiliary amine, and
      ii) a distillation residue consisting essentially of a second polyamine fraction, and
   e) recycling said first fraction as at least a portion of said hydrophobic solvent phase.

2. A process for the fractionation and purification of aromatic polyamine mixtures which is characterized in that
   a) the polyamine starting mixture (A) is distributed, with intermixing of the phases, in a two-phase system comprising (i) a hydrophobic solvent phase (B) which comprises substantially hydrophobic solvent and optionally an aromatic auxiliary amine which is virtually insoluble in water and exhibits at normal pressure a boiling point which is at least 20° C. below the boiling point of the lowest-boiling component of the starting mixture and at least 20° C. above the boiling point of the solvent, and optionally polyamine, and (ii) an aqueous phase (C) comprising substantially water, a strong acid and optionally auxiliary amine present at least in part in the salt form, and optionally polyamines present at least in part in the salt form, with the use as an aid of an extraction stage (7) operating on the countercurrent principle, in that the starting polyamine mixture is introduced into the extraction stage (7) with the aqueous phase, with the proviso that in this two-phase system the sum of the amine equivalents introduced in streams (A), (B) and (C) always exceeds the number of acid equivalents introduced in stream (C), the organic phase (D) leaving this extraction stage (7) is, b) optionally at least in part by way of an interposed extraction stage (6) and/or c) optionally with separation of a partial stream upstream or downstream of the extraction stage (6) which is optionally passed through and return of the separated partial stream to the extraction stage (7) and/or to the optionally present extraction stage (6) by way of an extraction stage (5) positioned upstream, d) separated in an optionally multi-stage distillation (11.1), (11.2) into a first fraction (E) which is recycled in extraction stage (7), comprising substantially hydrophobic solvent and optionally auxiliary amine, optionally a second fraction (F) comprising substantially auxiliary amine and optionally hydrophobic solvent, and a distillation residue (G) comprising substantially a first polyamine fraction, and e) the aqueous phase (H) leaving the extraction stage (7) is guided into a neutralization stage (8), the acid contained in the aqueous phase is neutralized with bases, preferably aqueous sodium hydroxide, and is then separated mechanically in a phase separation step into an aqueous phase containing the acid in the form of its neutral salts, and an organic phase containing substantially polyamine, optionally auxiliary amine and optionally hydrophobic solvent, and f) the organic phase (J) arising in the neutralization stage (8) is, optionally after passing through a washing stage (9), worked up at least in part in a distillation stage (12) into a distillation fraction (K) containing the proportions of hydrophobic solvent contained in (J) and the auxiliary amine optionally contained, and a second polyamine fraction arising as the distillation residue (L).

3. The process of claim 2, wherein b) the organic phase (D) arising in the extraction stage (7) is extracted at least in part in an interposed extraction stage (6), in countercurrent, with at least a part volume of the aqueous acid (stream (X)) and/or optionally water from stream (Y) and/or optionally auxiliary amine and/or is extracted in countercurrent with at least a part volume, preferably with the total volume, of the aqueous phase (Q) arising in the optionally present extraction stage (5) positioned upstream, the aqueous phase (N) resulting in the interposed extraction stage (6) is supplied to the extraction stage (7), and the organic phase (O) arising in the interposed extraction stage (6) is supplied to the working-up stage (11).

4. The process of claim 2, wherein c) a partial stream of the organic phase (D) leaving the extraction stage (7) and/or a partial stream of the organic phase (O) leaving the optionally present interposed extraction stage (6) is separated and in an extraction stage (5) positioned upstream is extracted in countercurrent with at least a part volume of the aqueous acid available as stream (X), the organic stream (P) utilized in the extraction stage (5) is dimensioned such that there takes place in (5) as extensive a transfer as possible of the polyamine contained in the said organic stream into the aqueous phase (Q), the aqueous phase (Q) resulting in the extraction stage (5) positioned upstream is, optionally after the addition of water from stream (Y) and/or auxiliary amine, supplied to the extraction stage (6), and the organic phase (R) impoverished as to polyamine and arising in the extraction stage (5) positioned upstream, is supplied to the extraction stage (7) and/or to the optionally present extraction stage (6).

5. The process of claim 2, wherein aniline is used as the auxiliary amine.

6. The process of claim 2, wherein 2,6-dimethylaniline is used as the auxiliary amine.

7. The process of claim 2, wherein xylidine mixtures are used as the auxiliary amine.

8. The process of claim 2, wherein 2-methyl-6-ethylaniline is used as the auxiliary amine.

9. The process of claim 2, wherein a polyamine mixture produced by acid-catalyzed aniline/formaldehyde condensation is used as the polyamine mixture of the diphenylmethane series.

10. In a process for the preparation of aromatic polyisocyanates by the phosgenation of aromatic polyamines, the improvement wherein the aromatic polyamine is produced according to the process of claim 1.

11. In a process for the preparation of cycloaliphatic polyamines by the hydrogenation of aromatic polyamines, the improvement wherein the aromatic polyamine is produced according to the process of claim 1.

* * * * *